US009822312B2

(12) United States Patent
Bezemer et al.

(10) Patent No.: US 9,822,312 B2
(45) Date of Patent: Nov. 21, 2017

(54) METHOD FOR START-UP AND OPERATION OF A FISCHER-TROPSCH REACTOR

(71) Applicant: SHELL OIL COMPANY, Houston, TX (US)

(72) Inventors: Gerrit Leendert Bezemer, Amsterdam (NL); Carolus Matthias Anna Maria Mesters, Sugar Land, TX (US); Johan Peter Den Breejen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/126,364

(22) PCT Filed: Mar. 16, 2015

(86) PCT No.: PCT/EP2015/055421
§ 371 (c)(1),
(2) Date: Sep. 15, 2016

(87) PCT Pub. No.: WO2015/140099
PCT Pub. Date: Sep. 24, 2015

(65) Prior Publication Data
US 2017/0081593 A1 Mar. 23, 2017

(30) Foreign Application Priority Data
Mar. 17, 2014 (EP) .................... 14160190

(51) Int. Cl.
C10G 2/00 (2006.01)
C07C 1/04 (2006.01)
(Continued)

(52) U.S. Cl.
CPC .............. C10G 2/332 (2013.01); B01J 8/001 (2013.01); B01J 8/02 (2013.01); B01J 8/065 (2013.01);
(Continued)

(58) Field of Classification Search
CPC ... B01J 23/75; B01J 37/18; B01J 8/001; B01J 8/02; B01J 8/065; B01J 8/067;
(Continued)

(56) References Cited

U.S. PATENT DOCUMENTS 4,595,703 A 6/1986 Payne et al.
4,626,552 A 12/1986 Arcuri
(Continued)

FOREIGN PATENT DOCUMENTS

WO 9700231 1/1997

OTHER PUBLICATIONS

Jalama, K. et al. "Co/TiO2 Fischer-Tropsch catalyst activation by synthesis gas" Catalysis Communications 17 (2012) 154-159.*
(Continued)

Primary Examiner — Medihanit Bahta

(57) ABSTRACT

The invention relates to a method for start-up and operation of a Fischer-Tropsch reactor comprising the steps of: (a) providing a reactor with a fixed bed of reduced Fischer-Tropsch catalyst that comprises cobalt as catalytically active metal; (b) supplying a gaseous feed stream comprising carbon monoxide and hydrogen to the reactor, wherein the gaseous feed stream initially comprises a nitrogen-containing compound other than molecular nitrogen in an initial concentration in the range of from 0.1 to 50 ppmv based on the volume of the gaseous feed stream; (c) converting carbon monoxide and hydrogen supplied with the gaseous feed stream to the reactor into hydrocarbons at an initial reaction temperature, wherein the initial reaction temperature is set at a value of at least 200° C. and hydrocarbons are produced at a first yield; (d) maintaining the initial reaction temperature at the set value and maintaining the first yield by decreasing the concentration of the nitrogen-containing compound in the gaseous feed stream supplied to the reac-
(Continued)

tor; (e) optionally increasing the reaction temperature after the concentration of the nitrogen-containing compound in the gaseous feed stream has decreased to a value below 100 ppbv.

11 Claims, 2 Drawing Sheets

(51) Int. Cl.
    *B01J 37/18*     (2006.01)
    *B01J 23/75*     (2006.01)
    *B01J 8/06*     (2006.01)
    *B01J 8/00*     (2006.01)
    *B01J 8/02*     (2006.01)
    *B01J 23/94*     (2006.01)

(52) U.S. Cl.
    CPC ............... *B01J 8/067* (2013.01); *B01J 23/75* (2013.01); *B01J 23/94* (2013.01); *B01J 37/18* (2013.01); *C07C 1/04* (2013.01); *C07C 1/045* (2013.01); *C07C 1/047* (2013.01); *C07C 1/048* (2013.01); *C07C 1/0455* (2013.01); *C10G 2/341* (2013.01); *B01J 2208/00061* (2013.01); *B01J 2208/00628* (2013.01); *B01J 2208/00646* (2013.01); *B01J 2208/00716* (2013.01); *B01J 2219/002* (2013.01); *B01J 2219/00213* (2013.01); *B01J 2219/00231* (2013.01)

(58) Field of Classification Search
    CPC .... B01J 2208/00061; B01J 2208/00628; B01J 2208/00646; B01J 2208/00716; B01J 2219/002; B01J 2219/00213; B01J 2219/00231; B01J 23/94; C10G 2/332; C10G 2/341
    See application file for complete search history.

(56) References Cited

U.S. PATENT DOCUMENTS

| | | | |
|---|---|---|---|
| 7,855,236 | B2 | 12/2010 | Van Hardeveld et al. |
| 2005/0049317 | A1 | 3/2005 | Raje et al. |
| 2005/0154069 | A1 | 7/2005 | Inga et al. |
| 2005/0227866 | A1 | 10/2005 | Berge et al. |
| 2007/0287759 | A1 | 12/2007 | Visagie et al. |
| 2008/0262112 | A1 | 10/2008 | Marion et al. |
| 2008/0275144 | A1 | 11/2008 | Van Hardeveld et al. |
| 2011/0160510 | A1 | 6/2011 | Claeys et al. |
| 2012/0202899 | A1 | 8/2012 | Visagie et al. |

OTHER PUBLICATIONS

Periodic Table of Elements; IUPAC version; 87th Edition of the Handbook of Chemistry and Physics (CRC Press); 1 page.
International Search Report for PCT/EP2015/055421 dated Jul. 14, 2015; 5 pages.

\* cited by examiner

METHOD FOR START-UP AND OPERATION OF A FISCHER-TROPSCH REACTOR

PRIORITY CLAIM

The present application is the National Stage (§371) of International Application No. PCT/EP2015/055421, filed Mar. 16, 2015, which claims priority from European Patent Application No. 14160190.6, filed Mar. 17, 2014, incorporated herein by reference.

FIELD OF THE INVENTION

The present invention relates to a method for start-up and operation of a Fischer-Tropsch reactor containing a Fischer-Tropsch catalyst, wherein at least during start-up of the reactor the activity of the catalyst is decreased.

The catalyst is suitable for use in producing normally gaseous, normally liquid and optionally solid hydrocarbons from synthesis gas generally provided from a hydrocarbonaceous feed, in a Fischer-Tropsch process. In the current specification such a catalyst is referred to as a Fischer-Tropsch catalyst.

BACKGROUND TO THE INVENTION

The Fischer-Tropsch process can be used for the conversion of synthesis gas into liquid and/or solid hydrocarbons. The synthesis gas may be obtained from hydrocarbonaceous feedstock in a process wherein the feedstock, e.g. natural gas, associated gas and/or coal-bed methane, heavy and/or residual oil fractions, coal, biomass, is converted in a first step into a mixture of hydrogen and carbon monoxide. This mixture is often referred to as synthesis gas or syngas. The synthesis gas is then fed into a reactor where it is converted in one or more steps over a suitable catalyst at elevated temperature and pressure into paraffinic compounds and water in the actual Fischer-Tropsch process. The obtained paraffinic compounds range from methane to high molecular weight modules. The obtained high molecular weight modules can comprise up to 200 carbon atoms, or, under particular circumstances, even more carbon atoms. Numerous types of reactor systems have been developed for carrying out the Fischer-Tropsch reaction. For example, Fischer-Tropsch reactor systems include fixed bed reactors, especially multi-tubular fixed bed reactors, fluidised bed reactors, such as entrained fluidised bed reactors and fixed fluidised bed reactors, and slurry bed reactors such as three-phase slurry bubble columns and ebulated bed reactors.

Catalysts used in the Fischer-Tropsch synthesis often comprise a carrier-based support material and one or more metals from Group 8-10 of the Periodic Table of Elements, especially from the cobalt or iron groups, optionally in combination with one or more metal oxides and/or metals as promoters selected from zirconium, titanium, chromium, vanadium and manganese, especially manganese. Such catalysts are known in the art and have been described for example, in the specifications of WO 9700231A and U.S. Pat. No. 4,595,703.

US2005/0154069 discloses a Fischer-Tropsch synthesis process in a slurry reactor.

One of the limitations of a Fischer-Tropsch process is that the activity of the catalyst will, due to a number of factors, decrease over time. The activity of the catalyst is decreased as compared to its initial catalytic activity. The initial activity of the catalyst can be its activity when fresh prepared. A catalyst that shows a decreased activity after use in a Fischer-Tropsch process is sometimes referred to as deactivated catalyst, even though it usually still shows activity. Sometimes such a catalyst is referred to as a deteriorated catalyst. Sometimes it is possible to regenerate the catalyst. This may be performed, for example, with one or more oxidation and/or reduction steps.

After regeneration, catalysts often show an activity that is lower than the activity of fresh prepared catalysts. Especially after multiple regenerations, it often proofs hard to regain an activity level comparable to the activity of fresh prepared catalysts. In order to be able to use a catalyst for a long time, it thus may be desirable to start a Fischer-Tropsch process with a fresh catalyst that has a relatively high activity.

The use of fresh or rejuvenated catalysts with a relatively high initial activity may have disadvantages. This may especially be the case when the amount of catalyst used in a reactor tube is fixed after loading of the catalyst in the reactor tube. One example of a reactor tube filled with a fixed amount of catalyst is a reactor tube filled with a packed bed of catalyst particles.

In a Fischer-Tropsch process with a catalyst with a relatively high initial activity, the activity of the catalyst is especially high at the start of the process. And, due to the high activity of the catalyst, a lot of water is produced in the Fischer-Tropsch hydrocarbon synthesis, resulting in a high relative humidity at the start of the Fischer-Tropsch process. During Fischer-Tropsch synthesis the relative humidity in a reactor tube may increase to such a level that it accelerates the deactivation of the catalyst during use. During start-up of a Fischer-Tropsch reactor with a very active catalyst, the reaction temperature is typically kept at a relatively low value, e.g. below 200° C., in order to avoid a too high product yield and accompanying high temperature rise due to the exothermic reaction. Without wishing to be bound to any theory, it is believed that especially the combination of relatively low temperature and a relatively high yield results in a high relative humidity in the reactor and therewith in undesired irreversible catalyst deactivation.

Therefore, especially in the start-up phase of a Fischer Tropsch reactor with a catalyst with a relatively high activity, the deactivation of the catalyst takes place at a relatively high rate. Deactivation due to relative humidity proofed to be difficult to reverse. The high initial activity in such a case is thus quickly lost, whereas regeneration procedures have only a limited effect.

SUMMARY OF THE INVENTION

It is an object of the present invention to provide an improved Fischer-Tropsch process in which a cobalt catalyst is used that has a relatively high initial activity. Especially the start-up of a Fischer-Tropsch reactor is improved. Preferably, also the start-up of a Fischer-Tropsch reactor after a regeneration step is improved.

It has now been found that the conditions of relative humidity and therewith of increased catalyst deactivation at the start-up of a Fischer-Tropsch reactor that has been loaded with fresh or rejuvenated catalyst can be avoided by supplying a feed gas stream comprising a nitrogen-containing compound other than molecular nitrogen to the catalyst in the initial stages of operation of the Fischer-Tropsch reactor. By supplying a nitrogen-containing compound to the freshly prepared or rejuvenated reduced catalyst, the catalyst activity is decreased and the temperature can be increased. Such conditions of higher temperature and decreased activity result in a lower relative humidity and less catalyst deactivation.

Further C5+ selectivity is decreased at start up. The inventors have found that although activity and C5+ selectivity are sacrificed at the beginning of the Fischer-Tropsch process, this sacrifice will be compensated since activity and selectivity will remain constant and will be at higher levels than for processes according to the prior art after a prolonged amount of time.

Moreover, since the effect of such nitrogen-containing compound on catalyst activity seems to be reversible, the catalyst activity can be tuned by adjusting the concentration of the nitrogen-containing compound. In particular, the gradual decrease in catalyst activity can be compensated by gradually decreasing the concentration of the nitrogen-containing compound in the feed gas stream supplied to the catalyst. Thus, reaction temperature and reactor productivity (yield) can be controlled and kept constant during a relatively long period after start-up of the reactor, resulting in improved catalyst stability.

Accordingly, the present invention relates to a method for start-up and operation of a Fischer-Tropsch reactor comprising the steps of:

(a) providing a reactor with a fixed bed of reduced Fischer-Tropsch catalyst that comprises cobalt as catalytically active metal;
(b) supplying a gaseous feed stream comprising carbon monoxide and hydrogen to the reactor, wherein the gaseous feed stream initially comprises a nitrogen-containing compound other than molecular nitrogen in an initial concentration in the range of from 0.1 to 50 ppmv based on the volume of the gaseous feed stream;
(c) converting carbon monoxide and hydrogen supplied with the gaseous feed stream to the reactor into hydrocarbons at an initial reaction temperature, wherein the initial reaction temperature is set at a value of at least 200° C. and hydrocarbons are produced at a first yield;
(d) maintaining the initial reaction temperature at the set value and maintaining the first yield by decreasing the concentration of the nitrogen-containing compound in the gaseous feed stream supplied to the reactor;
(e) optionally increasing the reaction temperature after the concentration of the nitrogen-containing compound in the gaseous feed stream has decreased to a value below 100 ppbv.

An important advantage of the method of the invention is that a higher reaction temperature is allowed in the start-up phase and the initial phase of the operation of the reactor, compared to the initial reaction temperature in a reactor wherein no nitrogen-containing compound is supplied with the feed gas stream, resulting in a lower relative humidity. Another advantage is that by tuning the amount of nitrogen-containing compound, the reaction temperature and/or the yield can be controlled. It has further been found that the selectivity for C5+ hydrocarbons is not importantly affected by the higher reaction temperature during start-up and initial phase of operation of the reactor.

Another advantage of the method according to the invention is that, compared to start-up methods wherein a relatively low initial temperature is used to avoid a too high yield and water production of the reactor at or shortly after start-up, heat recovery from the process is improved, since steam of a higher quality can be produced.

Another advantage is that the catalyst can be utilized for a prolonged amount of time before regeneration of the catalyst is required.

DETAILED DESCRIPTION OF THE INVENTION

Figure 1:
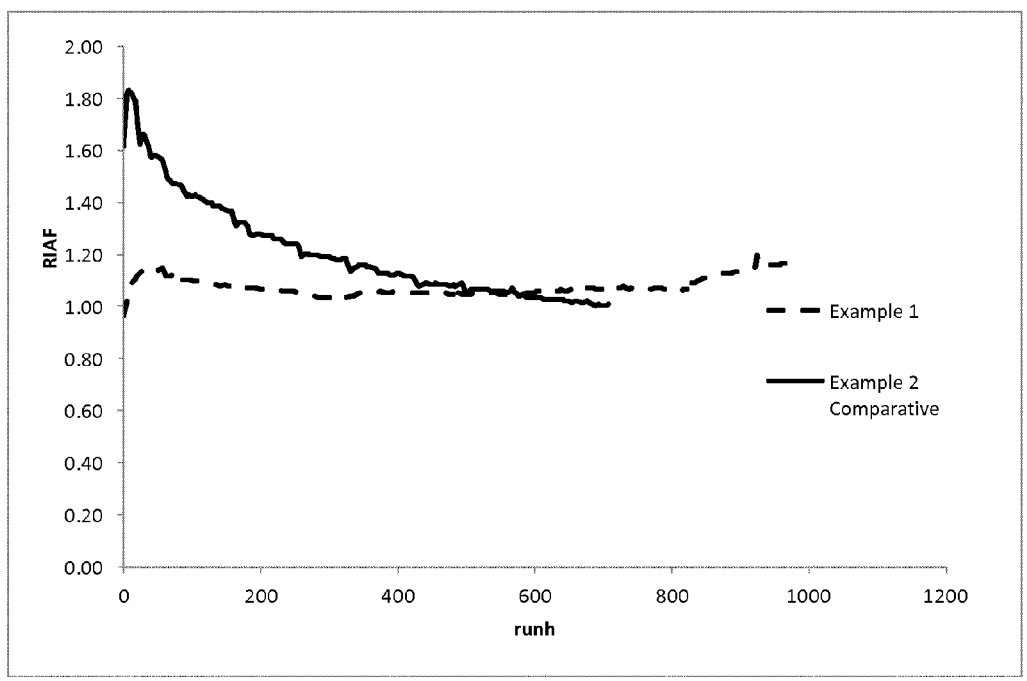
FIG. 1 shows the relative intrinsic activity factor (RIAF) over time for Example 1 and comparative Example 2.

The method according to the invention is a method for start-up and operation of a Fischer-Tropsch reactor. The method comprises a first step of providing a reactor with a fixed bed of reduced Fischer-Tropsch catalyst. The catalyst comprises cobalt as catalytically active metal.

The catalyst may be a fresh catalyst or a rejuvenated catalyst. Reference herein to a fresh catalyst is to a freshly prepared catalyst that has not been subjected to a Fischer-Tropsch process. Reference herein to a rejuvenated catalyst is to a regenerated catalyst of which the initial activity has been at least partially restored, typically by means of several reduction and/or oxidation steps. The catalyst is preferably a fresh catalyst, since in particular fresh catalysts have a very high initial activity.

The catalyst comprises cobalt as catalytically active metal. Fischer-Tropsch catalysts comprising cobalt as catalytically active metal are known in the art. Any suitable cobalt-comprising Fischer-Tropsch catalysts known in the art may be used. Typically such catalyst comprises cobalt on a carrier-based support material, optionally in combination with one or more metal oxides and/or metals as promoters selected from zirconium, titanium, chromium, vanadium and manganese, especially manganese. A most suitable catalyst comprises cobalt as the catalytically active metal and titania as carrier material.

The catalyst may further comprise one or more promoters. One or more metals or metal oxides may be present as promoters, more particularly one or more d-metals or d-metal oxides. Suitable metal oxide promoters may be selected from Groups 2-7 of the Periodic Table of Elements, or the actinides and lanthanides. In particular, oxides of magnesium, calcium, strontium, barium, scandium, yttrium, lanthanum, cerium, titanium, zirconium, hafnium, thorium, uranium, vanadium, chromium and manganese are suitable promoters. Suitable metal promoters may be selected from Groups 7-10 of the Periodic Table of Elements. Manganese, iron, rhenium and Group 8-10 noble metals are particularly suitable as promoters, and are preferably provided in the form of a salt or hydroxide.

The promoter, if present in the catalyst, is typically present in an amount of from 0.001 to 100 parts by weight per 100 parts by weight of carrier material, preferably 0.05 to 20, more preferably 0.1 to 15. It will however be appreciated that the optimum amount of promoter may vary for the respective elements which act as promoter.

A most suitable catalyst comprises cobalt as the catalytically active metal and zirconium as a promoter. Another most suitable catalyst comprises cobalt as the catalytically active metal and manganese and/or vanadium as a promoter. If the catalyst comprises cobalt as the catalytically active metal and manganese and/or vanadium as promoter, the cobalt: (manganese+vanadium) atomic ratio is advantageously at least 12:1.

It has been found that the method according to the invention is particularly suitable for start-up and operation of a Fischer-Tropsch reactor containing a catalyst without a noble metal as promoter. Therefore, the catalyst preferably does not comprise a noble metal.

References to "Groups" and the Periodic Table as used herein relate to the new IUPAC version of the Periodic Table of Elements such as that described in the 87th Edition of the Handbook of Chemistry and Physics (CRC Press).

In step (a) a reactor is provided with a fixed bed of the catalyst, preferably with a fixed bed of catalyst particles, more preferably in a multi-tubular fixed bed reactor configuration.

The reactor is provided with a fixed bed of reduced catalyst in step (a). In a reduced catalyst the cobalt is essentially in its metallic state. The reactor may be provided with a fixed bed of reduced catalyst by reducing a fixed bed of catalyst precursor in-situ, i.e. in the same reactor wherein the Fischer-Tropsch hydrocarbon synthesis will take place, or by loading the reactor with a reduced catalyst that has for example be prepared by reducing a catalyst precursor in a separate vessel or reactor prior to loading the reduced catalyst in the reactor. Preferably the reactor is provided with a fixed bed of reduced catalyst by reducing a fixed bed of catalyst precursor in-situ.

Reference herein to a catalyst precursor is to a precursor that can be converted into a catalytically active catalyst by subjecting the precursor to reduction, usually by subjecting the precursor to hydrogen or a hydrogen-containing gas using reducing conditions. Such reduction step is well-known in the art.

Once the reactor is provided with a fixed bed of reduced Fischer-Tropsch catalyst in step (a), Fischer-Tropsch hydrocarbon synthesis is started in steps (b) and (c) by supplying a gaseous feed stream comprising carbon monoxide and hydrogen to the reactor. The gaseous feed stream comprises a nitrogen-containing compound other than molecular nitrogen in an initial concentration in the range of from 0.2 to 50 ppmv based on the total volume of the gaseous feed stream. The gaseous feed stream may be supplied to the reactor at any suitable gas hourly space velocity. In step (c) carbon monoxide and hydrogen in the gaseous feed stream supplied to the reactor are converted into hydrocarbons at a suitable reaction pressure and at an initial reaction temperature. The initial reaction temperature is set at a value of least 200° C., preferably at least 203° C., more preferably at a value in the range of from 205 to 220° C., even more preferably of from 210 to 215° C., and hydrocarbons are produced at a first yield (reactor productivity).

The first yield is the desired reactor productivity and is preferably in the range of from 75 to 500 grams hydrocarbons per liter of catalyst per hour, more preferably in the range of from 100 to 350 grams hydrocarbons per liter of catalyst per hour.

The presence of the nitrogen-containing compound reduces the (intrinsic) activity of the catalyst. Due to this lower activity, the initial reaction temperature required to achieve a desired yield can be set at a relatively high value. A combination of relatively high activity and relatively low temperature is therewith avoided. Such combination would result in a high yield and thus high water production at relatively low temperature and therewith to undesirably high relative humidity and irreversible catalyst deactivation.

Reference herein to activity of the catalyst is to the intrinsic activity of the catalyst. It is thus a property of the catalyst and not dependent on the actual reaction conditions applied.

Reference herein to yield is to the reactor productivity or space time yield, i.e. to the amount of hydrocarbons produced per volume of catalyst per hour.

Reference herein to the reaction temperature is to the temperature of coolant, typically cooling water, surrounding the fixed bed of catalyst.

Reference herein to the gaseous feed stream to the reactor is to the combined feed stream to the reactor including any gaseous recycle stream.

It will be appreciated that for a catalyst with a given activity, and for given conditions such as pressure, gas hourly space velocity and reactor configuration, reaction temperature and yield (reactor productivity) are directly related. If the reactor productivity is to be set at a certain value, reaction temperature is a resulting parameter and vice versa.

In the process according to the invention, the initial activity of the catalyst is tuned by adjusting the initial amount of nitrogen-containing compound in the gaseous feed stream. The initial activity is tuned such that the initial reaction temperature needed to achieve a desired first yield is sufficiently high to avoid a combination of low reaction temperature and high yield resulting in a high relative humidity in the reactor that might be detrimental for the stability of the catalyst, i.e. would result in irreversible and/or rapid catalyst deactivation.

During operation of a Fischer-Tropsch process, the catalyst is typically gradually deactivated. In prior art Fischer-Tropsch processes, such loss in activity is usually compensated by gradually increasing the reaction temperature. In the method according to the invention, the reaction temperature is, after start-up steps (b) and (c), maintained at the value at which it is initially set whilst maintaining the first yield, i.e. maintaining the yield of hydrocarbons at the same level as during start-up step (c). This is done by decreasing, preferably gradually decreasing, the concentration of the nitrogen-containing compound in the gaseous feed stream supplied to the reactor. By decreasing such concentration, the loss of activity of the catalyst is compensated by decreasing catalyst poisoning by the nitrogen-containing compound.

The concentration of the nitrogen-containing compound may be stepwise or continuously decreased. Reference herein to gradually decreasing is to continuously decreasing or to stepwise decreasing the concentration in at least two steps. The concentration is decreased such that the first yield, i.e. the yield at which hydrocarbons are produced in initial conversion step (c) is maintained at the maintained initial reaction temperature. Reference herein to maintaining the initial reaction temperature is to maintaining the reaction temperature at a level within 3° C. of the initial reaction temperature, i.e. in a range between 3° C. below and 3° C. above the initial reaction temperature. Reference herein to maintaining the first yield is to maintaining the yield within 10% of the first yield, i.e. in a range of from 90 to 110% of the first yield.

After a certain time of operation of the Fischer-Tropsch reactor, the activity might have been decreased so far that the first yield cannot be maintained at the set value of the initial reaction temperature by further decreasing the concentration of nitrogen-containing compound in the gaseous feed stream. Optionally, the reaction temperature is then increased to compensate for the loss in catalyst activity.

The method according to the invention therefore comprises an optional step (e) wherein the reaction temperature is increased after the concentration of the nitrogen-containing compound in the gaseous feed stream has decreased to a level from which further decreasing is not possible or impractical. This typically occurs when the concentration of the nitrogen-containing compound in the synthesis gas has already decreased to a concentration of or below 0.1 ppmv (100 ppbv), preferably below 0.01 ppmv (10 ppbv).

The conversion of carbon monoxide and hydrogen into hydrocarbons in steps (c), (d) and optional step (e) may be carried out at any reaction pressure and gas hourly space velocity known to be suitable for Fischer-Tropsch hydrocarbon synthesis. Preferably, the reaction pressure is in the range of from 10 to 100 bar (absolute), more preferably of from 20 to 80 bar (absolute). The gas hourly space velocity is preferably in the range of from 500 to 25,000 $h^{-1}$, more preferably of from 900 to 15,000 $h^{-1}$, even more preferably of from 1,300 to 8,000 $h^{-1}$. Preferably, the reaction pressure and the gas hourly space velocity are kept constant in steps (c), (d) and optional step (e).

The nitrogen-containing compound may be any nitrogen-containing compound other than molecular nitrogen that is gaseous under the process conditions applied. Examples of suitable nitrogen-containing compounds are ammonia, HCN, NO, amines, organic cyanides (nitriles), or heterocyclic compounds containing at least one nitrogen atom as ring member of a heterocyclic ring. Preferably, the nitrogen-containing compound is ammonia, HCN, NO or an amine. Preferred amines include amines with one or more alkyl or alcohol groups having up to five carbon atoms. More preferably, the amine is a mono-amine. Examples of especially preferred amines include trimethylamine, dipropylamine, diethanolamine, and methyl-diethanolamine. A particularly preferred nitrogen-containing compound is ammonia.

The initial concentration of the nitrogen-containing compound in the gaseous feed stream is in the range of from 0.1 to 50 ppmv, preferably of from 0.2 to 20 ppmv, more preferably of from 0.5 to 15 ppmv, even more preferably of from 1 to 10 ppmv.

The nitrogen-containing compound may be added to the gaseous feed stream or may be present in the gaseous feed stream as contaminant. If added, then the concentration of the nitrogen-containing compound may be decreased by adding less of such compound. If present as contaminant, then the concentration of the nitrogen-containing compound may be decreased by mixing different streams to form the (combined) gaseous feed stream, i.e. with different concentrations of nitrogen-containing contaminants.

Without wishing to be bound to any theory, it is believed that the nitrogen-containing compound effects reversible poisoning of the catalyst. At the initial contact of the reduced catalyst provided in step (a) with gaseous feed stream comprising nitrogen-containing compound, it may take a certain time before the poisoning effect and therewith the desired initial decrease in catalyst activity has been achieved. This implies that it might be necessary to operate during a short time period at a temperature that is lower than the desired set value of the initial temperature, in order to avoid a too high yield and/or to avoid the risk of a temperature trip in the very initial stage of operating the reactor.

In has further been found that a sufficient degree of catalyst poisoning, and therewith a sufficient decrease in activity of the catalyst, can be achieved from the start of step (b) of the method by providing in step (a) the reactor with a fixed bed of reduced catalyst by means of in-situ reduction of a fixed bed of catalyst precursor, i.e. of non-reduced catalyst, in the presence of ammonia. Such in-situ reduction in the presence of ammonia may be carried out by contacting the fixed bed of catalyst precursor in-situ, i.e. after loading the fixed bed of catalyst precursor in the reactor, under reducing conditions with a reducing gas comprising ammonia. Alternatively, the loaded fixed bed of catalyst precursor may be in-situ reduced by contacting the loaded catalyst precursor under reducing conditions with a reducing gas comprising nitrogen. It has been found that under these conditions, nitrogen is in-situ converted into ammonia.

Accordingly, the reactor is preferably provided with reduced catalyst by contacting a fixed bed of catalyst precursor in-situ with a hydrogen-containing gas comprising ammonia or nitrogen at a reduction temperature and pressure. The reduction temperature and pressure may be any suitable reduction temperature and pressure. Suitable reduction temperatures and pressures are known in the art and typically comprise a temperature in the range of from 220° C. to 450° C., preferably of from 240° C. to 350° C. and a pressure in the range of from 0.1 bar (absolute) to the pressure at which the Fischer-Tropsch reactor is to be operated, more preferably of from 0.2 bar (absolute) to 60 bar (absolute), even more preferably of from 1 bar (absolute) to 20 bar (absolute). The gas hourly space velocity of the hydrogen-containing gas during in-situ reduction with added or in-situ formed ammonia is preferably in the range of from 1-1,000 $h^{-1}$, more preferably of from 1-500 $h^{-1}$. Preferably, the hydrogen-containing gas comprises ammonia in a concentration in the range of from 2 to 1000 ppmv, more preferably in the range of from 5 to 100 ppmv, or nitrogen in a concentration in the range of from 0.1 to 90 vol %, more preferably of from 1 to 60 vol %, even more preferably of from 10 to 50 vol %, based on the total volume of hydrogen-containing gas. Preferably, ammonia or nitrogen is present in the hydrogen-comprising reducing gas during only a part of the contacting of the catalyst precursor with the hydrogen-comprising reducing gas, more preferably only at the end of the reduction period, more preferably during at most 50 hours, even more preferably during at most 40 hours.

Without wishing to be bound to any theory it is believed that under typical reduction conditions of temperature and pressure, and in the presence of a solid catalytic surface, hydrogen and nitrogen react to form ammonia. Under the reduction conditions applied, the Fischer-Tropsch catalyst and/or the metallic reactor wall may serve as solid catalytic surface. The in-situ formed ammonia will serve as poison for the Fischer-Tropsch catalyst and therewith suppress the catalyst activity even prior to supplying the gaseous feed stream comprising carbon monoxide and hydrogen to the catalyst. Thus, an initial stage with a too active catalyst can be prevented.

The method according to the invention may be applied for the start-up and further operation of a Fischer-Tropsch reactor with a fresh catalyst or with a regenerated catalyst. The method according to the invention is particularly suitable for a Fischer-Tropsch reactor containing a fresh catalyst.

It has been found that by using the method according to the invention, catalyst stability is improved in the sense that it takes longer until the activity of the catalyst has decreased to such a low level that rejuvenation of the catalyst is needed.

A Fischer-Tropsch process typically comprises more than one reactors. In a Fischer-Tropsch process with several reactors, the method according to the invention may be applied in only one or in only a part of the reactors, i.e. any reactor loaded with fresh catalyst or with rejuvenated catalyst.

The invention is illustrated by the following non-limiting examples.

EXAMPLES

Example 1

Invention

A cobalt-based Fischer-Tropsch catalyst was loaded in a reactor tube and reduced. Then synthesis gas to which ammonia was added such that the synthesis gas comprised 10 ppmv ammonia was supplied to the reduced catalyst. The initial reaction was set such that the resulting space time yield (STY) was 200 grams hydrocarbon products per litre catalyst per hour. The initial reaction temperature thus set was 215° C. The STY was maintained at a value of 200 g/l·h during 900 runhours by gradually decreasing the ammonia concentration until the ammonia concentration in the synthesis gas was 0.7 ppmv. Then the ammonia addition was stopped and the STY was maintained at 200 g/l·h by adjusting the reaction temperature. Immediately upon stopping the ammonia addition, the reaction temperature had to be decreased in order to maintain the STY at a value of 200 g/l·h. Subsequently, the reaction temperature had to be gradually increased to maintain STY at 200 g/l·h. At 300 runhours after stopping the ammonia addition, the experiment was stopped and the intrinsic activity of the catalyst was determined.

Example 2

Comparative

The experiment of Example 1 was repeated but now without addition of ammonia to the synthesis gas. As in experiment 1, the reactor productivity (STY) was maintained at a value of 200 g/l·h during the experiment.

The initial reaction temperature needed to set the reactor productivity (STY) at a value of 200 g/l·h was below 200° C. During the experiment the reaction temperature had to be gradually increased to maintain STY at 200 g/l·h. After 1,200 runhours, the experiment was stopped and the intrinsic activity of the catalyst was determined.

The intrinsic activity of the catalyst used in experiment 1 was 20% higher than the intrinsic activity of the catalyst used in comparative experiment 2. This shows that the method according to the invention results in improved catalyst stability compared to a process wherein no N-containing compound is used for suppressing the catalyst activity during start-up and the initial operation phase of the reactor.

Figure 2:
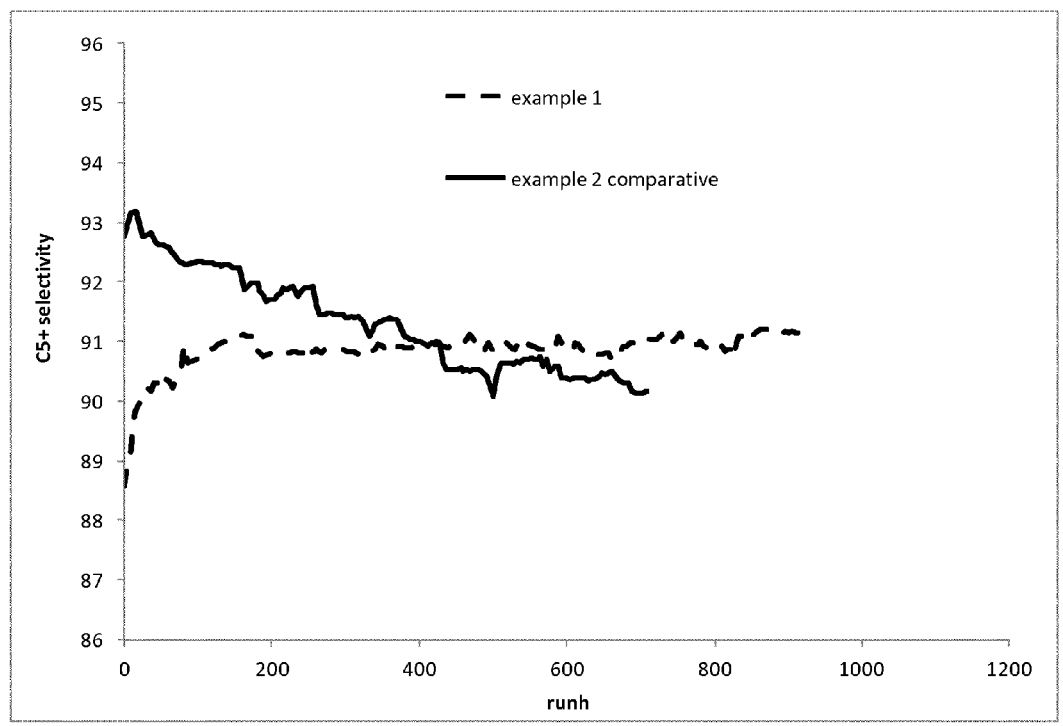
FIG. 2 shows the C5+ selectivity over time for Example 1 and comparative Example 2.

FIGS. 1 and 2 show the activity and C5+ selectivity as determined for Experiments 1 (interrupted line) and 2 (solid line) respectively. Both figures clearly show the initial sacrifice in activity and C5+ selectivity when using the Fischer-Tropsch method according to the invention (Example 1).

FIG. 1 clearly shows that at the start of the process according to the invention activity of the catalyst is less than for the process according to Example 2. However after running both processes for approximately 600 hours the activity of the catalyst can be maintained at a higher level with the process according to the present invention than with a method according to the prior art.

Similar results were observed when analyzing the C5+ selectivity as shown in FIG. 2. FIG. 2 shows the C5+ selectivity for the process according to Experiment 1 (interrupted line) and comparative Example 2 (solid line). Also for selectivity the sacrifice in selectivity at the beginning of the Fischer-Tropsch process according to the present invention is clearly visibly (compared to Example 2). As can be deduced from FIG. 2 after running the processes for approximately 400 hours selectivity can be maintained at a higher level with a method according to the present invention than with the method of Example 2.

Hence after running the Fischer-Tropsch synthesis according to the invention for a sufficient amount of time the benefit of a higher selectivity and activity compensates for the initial reduction of both.

Example 3

In order to test the ability of an amine to reversibly inactivate a cobalt-based Fischer-Tropsch catalyst, the following experiment was carried out.

A reduced cobalt-based Fischer-Tropsch catalyst was loaded in a reactor tube. Synthesis gas to which no N-containing compounds was added (less than 10 ppbv N-containing compounds) was supplied to the catalyst. The reactor productivity was set at a value of 200 g/l·h. Subsequently, trimethylamine was added to the synthesis gas that was supplied to the reduced catalyst in an amount that the trimethylamine concentration in the synthesis gas was 0.5 ppmv. The reaction temperature needed to maintain the reactor productivity had to be increased to 214° C. Subsequently, the addition of trimethylamine was stopped and the reaction temperature had to be decreased to about the initial reaction temperature in order to maintain the reactor productivity at 200 g/l·h. In the Table is shown the relative catalyst activities prior to trimethylamine addition, during trimethylamine addition, and after trimethylamine addition had been stopped. The results show that the decrease in catalyst activity due to addition of trimethylamine is reversible.

TABLE

Relative catalyst activity before, during and after trimethylamine (TMA) addition

| | Relative activity (%) |
|---|---|
| Before TMA addition | 100 |
| During TMA addition | 64 |
| After TMA addition | 97 |

That which is claimed is:

1. A method for start-up and operation of a Fischer-Tropsch reactor comprising the steps of:
   (a) providing a reactor with a fixed bed of reduced Fischer-Tropsch catalyst that comprises cobalt as catalytically active metal;
   (b) supplying a gaseous feed stream comprising carbon monoxide and hydrogen to the reactor, wherein the gaseous feed stream initially comprises a nitrogen-containing compound selected from the group consisting of ammonia, HCN, NO, an amine and combinations or two or more thereof, in an initial concentration in the range of from 0.1 to 50 ppmv based on the volume of the gaseous feed stream;
   (c) converting carbon monoxide and hydrogen supplied with the gaseous feed stream to the reactor into hydrocarbons at an initial reaction temperature, wherein the initial reaction temperature is set at a value of at least 200° C. and hydrocarbons are produced at a first yield;
   (d) maintaining the initial reaction temperature at the set value and maintaining the first yield by decreasing the concentration of the nitrogen-containing compound in the gaseous feed stream supplied to the reactor;

(e) optionally increasing the reaction temperature after the concentration of the nitrogen-containing compound in the gaseous feed stream has decreased to a value below 100 ppbv.

2. A method according to claim 1, wherein the catalyst is a fresh catalyst.

3. A method according to claim 1, wherein the nitrogen-containing compound is ammonia.

4. A method according to claim 1, wherein the initial reaction temperature is set at a value of at least 203° C.

5. A method according to claim 1, wherein the initial concentration of the nitrogen-containing compound is in the range of from 0.2 to 20 ppmv.

6. A method according to claim 1, wherein the concentration of the nitrogen-containing compound is gradually decreased in step (d).

7. A method according to claim 1, wherein the reactor is provided with a fixed bed of reduced catalyst in step (a) by reducing a fixed bed of catalyst precursor in the reactor.

8. A method according to claim 7, wherein the fixed bed of catalyst precursor is reduced by contacting the catalyst precursor with a hydrogen-containing gas comprising nitrogen or ammonia at a reduction temperature and pressure.

9. A method according to claim 8, wherein the hydrogen-containing gas comprises in the range of from 1 to 60 vol % nitrogen.

10. A method according to claim 8, wherein the hydrogen-containing gas comprises in the range of from 2 to 1,000 ppmv ammonia.

11. A method according to claim 1, wherein the catalyst does not comprise a noble metal.

* * * * *